(12) United States Patent
Wingen et al.

(10) Patent No.: US 7,026,021 B2
(45) Date of Patent: Apr. 11, 2006

(54) FLUORINATED HETEROCYCLES AND THEIR USE IN LIQUID-CRYSTAL MIXTURES

(75) Inventors: Rainer Wingen, Hofheim (DE); Barbara Hornung, Hasselroth (DE); Wolfgang Schmidt, Dreieich (DE)

(73) Assignee: Merck Patent GmbH, Darmstadt (DE)

( * ) Notice: Subject to any disclaimer, the term of this patent is extended or adjusted under 35 U.S.C. 154(b) by 6 days.

(21) Appl. No.: 10/903,937

(22) Filed: Jul. 30, 2004

(65) Prior Publication Data

US 2005/0056812 A1 Mar. 17, 2005

(30) Foreign Application Priority Data

Aug. 1, 2003 (DE) ............................. 103 36 023

(51) Int. Cl.
| | |
|---|---|
| C09K 19/34 | (2006.01) |
| C09K 19/32 | (2006.01) |
| C07D 307/77 | (2006.01) |
| C07D 307/93 | (2006.01) |
| C07C 23/08 | (2006.01) |

(52) U.S. Cl. ............. 428/1.1; 252/299.61; 252/299.62; 549/457; 570/129; 570/131; 570/183; 570/187

(58) Field of Classification Search ................ 428/1.1; 252/299.61, 299.62; 549/457; 570/129, 570/131, 183, 187
See application file for complete search history.

(56) References Cited

U.S. PATENT DOCUMENTS

| | | | | |
|---|---|---|---|---|
| 6,491,989 B1 * | 12/2002 | Manero et al. | ............... | 428/1.1 |
| 6,558,758 B1 | 5/2003 | Yanai et al. | | |
| 6,670,514 B1 * | 12/2003 | Wingen et al. | ............. | 570/129 |
| 6,737,125 B1 * | 5/2004 | Hornung et al. | ............. | 428/1.1 |
| 6,759,103 B1 * | 7/2004 | Hornung et al. | ............. | 428/1.1 |
| 6,793,984 B1 * | 9/2004 | Bremer et al. | ............. | 428/1.1 |
| 6,887,533 B1 * | 5/2005 | Schmidt et al. | ............. | 428/1.1 |

FOREIGN PATENT DOCUMENTS

| | | |
|---|---|---|
| DE | 100 50 071 A1 | 6/2001 |
| WO | WO 02/055463 A1 | 7/2002 |
| WO | WO 03/010120 A1 | 2/2003 |

OTHER PUBLICATIONS

Ichinose et al, High Optical Anisotropy and Small Rotational Viscosity LC Mixture for Field-Sequential Color TN-LCD's, Abstract LCT4-3, 2000, pp. 77 to 80.

* cited by examiner

Primary Examiner—Shean C. Wu
(74) Attorney, Agent, or Firm—Frommer Lawrence & Haug LLP

(57) ABSTRACT

Compounds of the general formula (I)

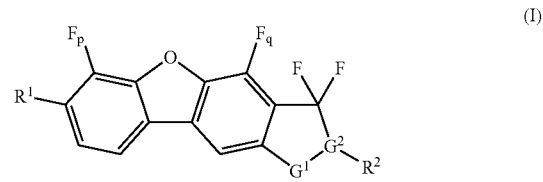

where:
$R^1$, $R^2$ are each independently
a) H
b) $-M^1-A^1-R^5$
c) a straight-chain or branched alkyl radical having from 1 to 16 carbon atoms or a straight-chain or branched alkenyl radical having from 2 to 16 carbon atoms, where
c1) one or more nonadjacent and nonterminal $CH_2$ groups may be replaced by —O—, —C(=O)O—, —O—C(=O)—, —O—C(=O)—O—, —C(=O)— or —Si(CH_3)_2—, and/or
c2) one $CH_2$ group may be replaced by —C≡C—, cyclopropane-1,2-diyl, cyclobutane-1,3-diyl, cyclohexane-1,4-diyl or phenylene-1,4-diyl, and/or
c3) one or more hydrogen atoms may be replaced by F and/or Cl,
p, q are each independently 0 or 1
$G^1$-$G^2$ is —$CH_2CH$—, —CH=C—, —$CH_2CH_2CH$— or —CH=CH—CH—
$M^1$ is —CO—O—, —O—CO—, —$CH_2$—O—, —O—$CH_2$—, —$CF_2$—O—, —O—$CF_2$—, —CH=CH—, —CF=CF—, —C≡C—, —$CH_2$—$CH_2$—CO—O—, —O—CO—$CH_2$—$CH_2$—, —$CH_2$—$CH_2$—, —$CF_2$—$CF_2$—, —$(CH_2)_4$—, —OC(=O)CF=CF— or a single bond,
$A^1$ is 1,4-phenylene where one or two hydrogen atoms may be replaced by F, Cl, CN and/or $OCF_3$, or up to three hydrogen atoms may be replaced by fluorine, 1,4-cyclohexylene where one or two hydrogen atoms may be replaced by $CH_3$ and/or F, 1-cyclohexene-1,4-diyl, where one hydrogen atom may be replaced by $CH_3$ or F, or 1,3-dioxane-2,5-diyl,
$R^5$ has the same possible definitions as $R^1$ and $R^2$, with the exception of -$M^1$-$A^1$-$R^5$
with the provisos that:
a) at least one of p, q is 1,
b) $R^1$ and $R^2$ must not at the same time be H.
are used in liquid-crystal mixtures.

9 Claims, 1 Drawing Sheet

FLUORINATED HETEROCYCLES AND THEIR USE IN LIQUID-CRYSTAL MIXTURES

An ever-increasing number of applications of LCDs, for example for use in cars, in which a temperature range of from −40° C. to 100° C. can quite possibly exist, but also for transportable units such as cellphones and notebook PCs, requires liquid-crystal mixtures which have firstly a very wide working temperature range and secondly a very low threshold voltage.

There is therefore a continuing demand for novel, suitable liquid-crystal mixtures and mixture components. As described in Ichinose et al. (IDW'00, Abstr. LCT4-3) or in DE-A 10050071, materials are sought in which there is coexistence of high optical anisotropy (Δn) and low rotational viscosity, although other parameters, for example high absolute values of dielectric anisotropy (Δε) are likewise required, in addition to further parameters relevant to the application.

Fluorinated benzofurans and dibenzofurans are disclosed by WO 02/055463 and WO 03/010120. However, since the manufacturers of liquid-crystal displays are interested in constantly improved liquid-crystal mixtures, there is a need for further components of liquid-crystal mixtures, with which individual parameters relevant to the application, for example the dielectric anisotropy (Δn) or the optical anisotropy (Δε) may be optimized.

It is therefore an object of the present invention to provide novel components for use in nematic or cholesteric or chiral-smectic liquid-crystal mixtures which have high absolute values of dielectric anisotropy combined with a favorable ratio of viscosity to clearing point. In addition, the compounds should preferably to a high degree be light- and UV-stable, and also thermally stable. In addition, they should be suitable for realizing a high voltage holding ratio (VHR). In addition, they should have good synthetic accessibility and therefore potentially be inexpensive.

Figure 1:
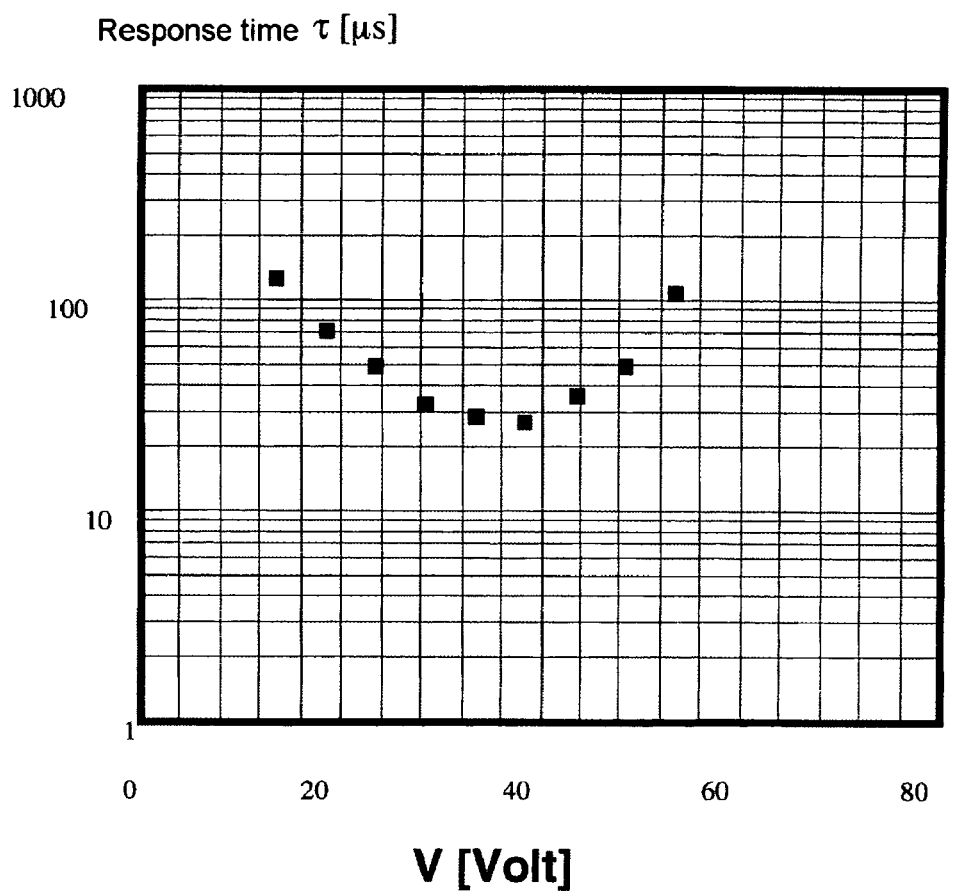
FIG. 1 shows the τVmin curve (τ plotted against the voltage) at Tc-30K, monopolar pulses and a cell separation of 1.3 μm.

According to the invention, the objects are achieved by compounds of the formula (I)

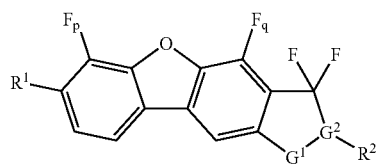

(I)

where:
$R^1$, $R^2$ are each independently
a) H
b) $-M^1-A^1-R^5$
c) a straight-chain or branched alkyl radical having from 1 to 16 carbon atoms or a straight-chain or branched alkenyl radical having from 2 to 16 carbon atoms, where
   c1) one or more nonadjacent and nonterminal $CH_2$ groups may be replaced by —O—, —C(=O)O—, —O—C(=O)—, —O—C(=O)—O—, —C(=O)— or —Si$(CH_3)_2$—, and/or
   c2) one $CH_2$ group may be replaced by —C≡C—, cyclopropane-1,2-diyl, cyclobutane-1,3-diyl, cyclohexane-1,4-diyl or phenylene-1,4-diyl, and/or
   c3) one or more hydrogen atoms may be replaced by F and/or Cl,
p, q are each independently 0 or 1, i.e. when the value is 0, —H is present at the position in question instead of —F,
$G^1$-$G^2$ is —$CH_2CH$—, —CH=C—, —$CH_2CH_2CH$— or —CH=CH—CH—
$M^1$ is —CO—O—, —O—CO—, —$CH_2$—O—, —O—$CH_2$—, —$CF_2$—O—, —O—$CF_2$—, —CH=CH—, —CF=CF—, —C≡C—, —$CH_2$—$CH_2$—CO—O—, —O—CO—$CH_2$—$CH_2$—, —$CH_2$—$CH_2$—, —$CF_2$—$CF_2$—, —$(CH_2)_4$—, —OC(=O)CF=CF— or a single bond,
$A^1$ is 1,4-phenylene where one or two hydrogen atoms may be replaced by F, Cl, CN and/or $OCF_3$, or up to three hydrogen atoms may be replaced by fluorine, 1,4-cyclohexylene where one or two hydrogen atoms may be replaced by $CH_3$ and/or F, 1-cyclohexene-1,4-diyl, where one hydrogen atom may be replaced by $CH_3$ or F, or 1,3-dioxane-2,5-diyl,
$R^5$ has the same possible definitions as $R^1$ and $R^2$, with the exception of -$M^1$-$A^1$-$R^5$, but is undependent of the definition of $R^1$ and $R^2$ with the provisos that:
a) at least one of p, q is 1,
b) $R^1$ and $R^2$ must not at the same time be H, and also by liquid-crystal mixtures comprising these compounds.

Preference is given to compounds of the formulae (Ia) to (Id)

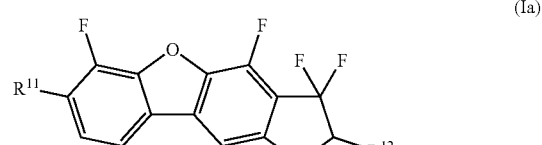

(Ia)

(Ib)

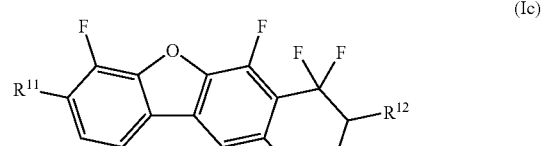

(Ic)

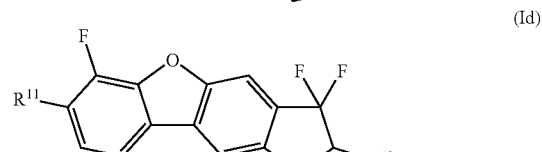

(Id)

where:
$R^{11}$ and $R^{12}$ are each independently hydrogen or an alkyl or alkyloxy radical having from 1 to 10 carbon atoms or an alkenyl or alkenyloxy radical having from 2 to 10 carbon atoms, where one or more hydrogen atoms may also each be replaced by F, or the $R^{15}$-$A^{15}$-$M^{15}$-moiety, with the provisos that:
$R^{11}$ and $R^2$ must not at the same time be hydrogen,
$R^{11}$ and $R^{12}$ must not at the same time be $R^{15}$-$A^{15}$-$M^{15}$,
$R^{15}$ is an alkyl or alkyloxy radical having from 1 to 10 carbon atoms or an alkenyl or alkenyloxy radical having from 2 to 10 carbon atoms
$A^{15}$ is phenylene-1,4-diyl, cyclohexane-1,4-diyl
$M^{15}$ is single bond, —C≡C—, —OCF$_2$—, —CF$_2$O—, —CF$_2$CF$_2$—, —CH$_2$CH$_2$—.

Particular preference, especially for use in nematic mixtures, is given to the compounds of the formula (Ia1) and (Ia2)

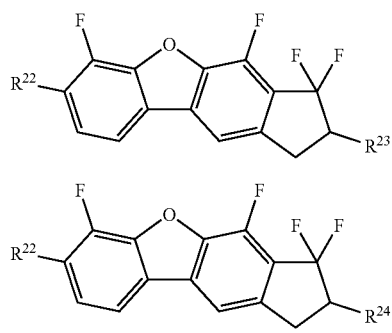

where:
$R^{22}$ and $R^{23}$ are each independently an alkyl or alkyloxy radical having from 1 to 6 carbon atoms or an alkenyl or alkenyloxy radical having from 2 to 5 carbon atoms,
$R^{24}$ is the $R^{15}$-$A^{15}$-$M^{15}$-moiety where
$R^{15}$ is an alkyl or alkyloxy radical having from 1 to 10 carbon atoms or an alkenyl or alkenyloxy radical having from 2 to 10 carbon atoms,
$A^{15}$ is phenylene-1,4-diyl, cyclohexane-1,4-diyl,
$M^{15}$ is a single bond or —CH$_2$CH$_2$—.

The provision of compounds of the formula (I) in a quite general sense considerably broadens the range of liquid-crystalline substances which are suitable for producing liquid-crystalline mixtures from different performance aspects.

In this context, the compounds of the formula (I) have a broad field of application. Depending on the selection of the substituents, they may be added to other classes of compound, in order, for example, to influence the dielectric and/or optical anisotropy of such a dielectric. They may also serve to optimize its threshold voltage and/or its viscosity. The compounds may also serve to increase the mesophase range or to adjust individual mesophases to parameters relevant to the application.

The compounds of the formula (I) are particularly suitable for influencing dielectric anisotropy (Δε) and/or the optical anisotropy Δn of liquid-crystal mixtures, even in small amounts in the mixture. The compounds of the formula (I) are particularly suitable for reducing the response time of ferroelectric liquid-crystal mixtures, even in small amounts in the mixture. The compounds of the formula (I) are likewise particularly suitable for adjusting the broadness of the S$_C$ or N phase to application requirements.

The present invention thus provides compounds of the formula (I) and also the use of these compounds as components of liquid-crystalline mixtures and liquid-crystalline mixtures comprising one or more compounds of the formula (I).

The compounds of the formula (I) may be used in various liquid-crystal mixtures, for example chiral-smectic, nematic or cholesteric. In the case of nematic mixtures, they are particularly suitable for active matrix displays (AM-LCD) (see, for example, C. Prince, Seminar Lecture Notes, Volume I, p. M-3/3–M-22, SID International Symposium 1997, B. B: Bahadur, Liquid Crystal Applications and Uses, Vol. 1, p. 410, World Scientific Publishing, 1990, E. Luider, Recent Progress of AMLCD's, Proceedings of the 15$^{th}$ International Display Research Conference, 1995, p. 9–12) and in-plane-switching displays (IPS-LCD), and, in the case of smectic liquid-crystal mixtures, for smectic (ferroelectric or antiferroelectric) displays. Further display possibilities are the ECB and VA display mode in the case of nematic and cholesteric LC mixtures.

Further components of liquid-crystal mixtures which comprise inventive compounds of the formula (I) are preferably selected from the known compounds having smectic and/or nematic and/or cholesteric phases. Mixture components suitable in this context are listed in particular in WO 00/36054, DE-A-19 531 165 and EP-A-0 893 424, which are explicitly incorporated herein by way of reference.

The present invention therefore also provides liquid-crystal mixtures, which comprise at least one compound of the formula (I), preferably in an amount of from 1 to 40% by weight, based on the liquid-crystal mixture. The mixtures preferably comprise at least 3 further components of smectic and/or nematic and/or cholesteric phases in addition to compounds of the formula (I). The invention additionally provides electrooptical display elements (liquid-crystal displays) which comprise the inventive mixtures.

Preference is given to displays which comprise the inventive nematic or smectic (ferroelectric or antiferroelectric) mixtures in combination with active matrix elements.

The inventive displays are typically constructed in such a way that one liquid-crystal layer is enclosed on both sides by layers which are typically, in this sequence starting from the LC layer, at least one alignment layer, electrodes and a boundary layer (for example of glass). In addition, they may comprise spacers, adhesive frames, polarizers and thin color filter layers for color displays. Further possible components are antireflection, passivation, compensation and barrier layers, and also electrically nonlinear elements such as thin-film transistors (TFT) and metal-insulator-metal (MIM) elements. The construction of liquid-crystal displays has already been described in detail in relevant monographs (see, for example, E. Kaneko, "Liquid Crystal TV Displays: Principles and Applications of Liquid Crystal Displays", KTK Scientific Publishers, 1987).

An example of a possible synthetic route to compounds of the formula (I) is specified in scheme 1 which follows, although other processes are also feasible and possible.

The following abbreviations are used:
n-BuLi n-butyllithium
DCC dicyclohexylcarbodiimide
DCM dichloromethane
DDQ 2,3-dichloro-5,6-dicyano-p-benzoquinone
DEAD diethyl azodicarboxylate (azodicarboxylic acid diethyl ester)
Diglyme diethylene glycol dimethyl ether
DMAP 4-(dimethylamino)pyridine
DME dimethoxyethane
DMF N,N-dimethylformamide
DMSO dimethyl sulfoxide
KOtBu potassium tert-butoxide
LICOR lithium organyl+potassium tert-butoxide LiTMP lithium 2,2,6,6-tetramethylpiperidide
MEK methyl ethyl ketone (2-butanone)
MTBE tert-butyl methyl ether
NMP N-methylpyrrolidone
4-TsOH 4-toluenesulfonic acid Scheme 1

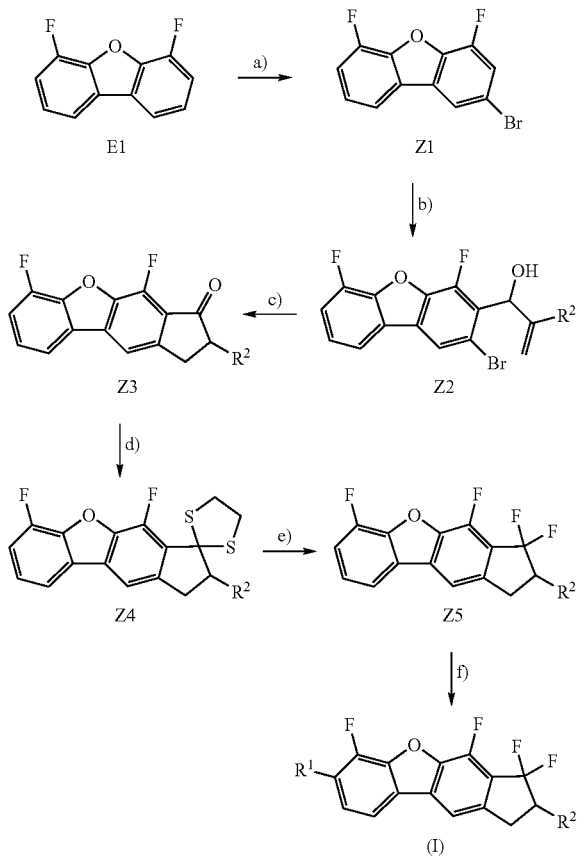

a) Br$_2$, CHCl$_3$ according to *Organikum*, 15th edition 1977, p. 393–394
b) 1. LDA 2. R$^2$—C(═CH$_2$)—CH═O according to WO 03/010120, p. 20
c) Pd catalyst, Et$_3$N according to WO 03/01020, p. 20
d) HSCH$_2$CH$_2$SH according to WO 03/01020, p. 21
e) Dibromohydantoin, HF-pyridine according to WO 03/01020, p. 22
f) 1. Metallation according to *J. Chem. Soc. Perkin Trans. I*, 1995, 2729,
2. Reaction with electrophile according to *Tetrahedron Lett.* 1996, 37, 6551

The reactant E1 is disclosed by the literature (WO 02/055463); the further starting materials (for example R$^2$-acroleins for stage b) are familiar to those skilled in the art (for example J. Chem Res. (S) 1980, 412 in the case that R$^2$=4-alkylcyclohexyl), and some are even commercially available.

Scheme 1 describes the synthesis of compound Z5. This may itself be an inventive compound of the formula (I), for example where R$^2$=4-alkylcyclohexyl and R$^1$=H. However, Z5 is also a central intermediate for the preparation of the inventive compounds. For instance, the electrophile (stage f) may, for example, be trialkyl borate; the boronic acid formed initially may then be converted by means of Suzuki couplings with the addition of R$^{15}$-A$^{15}$-Br to compounds (I) in which R$^1$ is the M$^{15}$-A$^{15}$-R$^{15}$ moiety where M$^{15}$=single bond and A$^{15}$=phenylene-1,4-diyl. However, the boronic acid may also be converted oxidatively to a compound (I) in which R$^1$ is OH; this OH group may be converted by standard methods of ether synthesis, for example Mitsunobu or Williamson reaction, to inventive compounds in which R$^1$ is an alkyloxy radical. When the electrophile used in stage f is an alkyl halide of the formula R$^1$—X, it is possible in this way to prepare from Z5 the compounds (I) where R$^1$=alkyl.

The invention is illustrated in detail by the examples which follow.

EXAMPLE 1

1,1,8,10-Tetrafluoro-7-propoxy-2-(4-propylcyclohexyl)-2,3-dihydro-1H-9-oxacyclopenta[b]fluorene

[Compound (I) where p=q=1, G$^1$-G$^2$=—CH$_2$CH—, R$^1$=OC$_3$H$_7$, R$^2$=4-propylcyclohexyl]

A solution of 2.1 g (5.8 mmol) of the compound Z5 where R$^2$=4-propylcyclohexyl (prepared according to the reaction sequence of scheme 1, using 1-(4-propylcyclohexyl)-acrolein in stage b) in 60 ml of tetrahydrofuran admixed at −75° C. with 1.1 equivalents of LDA. After a few minutes, 2 equivalents of trimethyl borate were added, and the mixture was brought to −30° C. and hydrolyzed at this temperature. After 10% hydrochloric acid had been added down to pH 4, extraction was effected twice with 100 ml each time of tert-butyl methyl ether, and the organic phases were combined, washed once each with 50 ml of saturated sodium chloride solution and water, and dried over sodium sulfate. The residue obtained after distilling off the solvent was dissolved in 70 ml of tert-butyl methyl ether, 3 equivalents of hydrogen peroxide (35%) were added and the mixture was stirred at 55° C. up to the end of the reaction. After customary workup (J. Chem. Soc., Perkin Trans. 1989, 2041–2053), purification was effected by chromatography (250 g of silica gel; dichloromethane/8:1 dichloromethane+ethyl acetate). The compound obtained after distilling off the solvent was dissolved in 30 ml of dichloromethane and admixed with in each case 1.1 equivalents of triphenylphosphine, diethyl azodicarboxylate and 1-propanol. On completion of reaction, the mixture was dried under reduced pressure and the residue purified by chromatography (100 g of silica gel, dichloromethane). After recrystallization from acetonitrile, 0.2 g of the target compound was obtained.

EXAMPLE 2

1,1,8,10-Tetrafluoro-7-heptyloxy-2-(4-propylcyclohexyl)-2,3-dihydro-1H-9-oxacyclopenta[b]fluorene

[Compound (I) where p=q=1, G$^1$-G$^2$=—CH$_2$CH—, R$^1$=OC$_7$H$_{15}$, R$^2$=4-propylcyclohexyl] is prepared in a similar manner to example 1, but using 1-heptanol (stage f).

USE EXAMPLE 1

A chiral-smectic C mixture consisting of

| | |
|---|---|
| 2-(4-Heptyloxyphenyl)-5-nonylpyrimidine | 19.6% |
| 5-Nonyl-2-(4-octyloxyphenyl)pyrimidine | 19.6% |
| 5-Nonyl-2-(4-nonyloxyphenyl)pyrimidine | 19.6% |
| 2-(2,3-Difluoro-4-heptyloxyphenyl)-5-nonylpyrimidine | 6.5% |
| 2-(2,3-Difluoro-4-octyloxyphenyl)-5-nonylpyrimidine | 6.5% |
| 2-(2,3-Difluoro-4-nonyloxyphenyl)-5-nonylpyrimidine | 6.5% |
| 5-Hexyloxy-2-(4-hexyloxyphenyl)pyrimidine | 19.6% |
| (S)-4-[4'-(2-Fluorooctyloxy)biphenyl-4-yl]-1-heptylcyclohexanecarbonitrile | 2.0% | is admixed with 5% of the compound from example 2.

This results in a mixture which, demonstrated by FIG. 1, is suitable for the operation of displays in inverse mode, since the curve profile has the required minimum and the values are within the technically relevant range.

USE EXAMPLE 2

A nematic mixture consisting of

| | |
|---|---|
| 4-[(1E)-1-Propenyl]-4'-propyl-1,1'-bicyclohexyl | 3.1% |
| Compound from example 1 | 5.0% |
| 4-[(4-Ethenyl)-1,1'-bicyclohexyl-4'-yl]methylbenzene | 5.2% |
| 1-Ethoxy-2,3-difluoro-4-[4-ethyl-1,1'-bicyclohexyl-4'yl]benzene | 6.1% |
| 1-Ethoxy-2,3-difluoro-4-[4-propyl-1,1'-bicyclohexyl-4'yl]benzene | 6.1% |
| 1-Ethoxy-2,3-difluoro-4-[4-pentyl-1,1'-bicyclohexyl-4'yl]benzene | 6.1% |
| 1-Methyl-2,3-difluoro-4-[4-ethyl-1,1'-bicyclohexyl-4'yl]benzene | 6.1% |
| 4-Ethyl-4'-(4-propylcyclohexyl)-1,1'-biphenyl | 8.4% |
| 1-Butoxy-2,3-difluoro-4-(4-propylcyclohexyl)benzene | 12.2% |
| 1-Ethoxy-2,3-difluoro-4-(4-pentylcyclohexyl)benzene | 12.2% |
| 1-Methyl-2,3-difluoro-4-[4-propyl-1,1'-bicyclohexyl-4'yl]benzene | 14.3% |
| 1-Butoxy-2,3-difluoro-4-(4-pentylcyclohexyl)benzene | 15.2% | has the following values, all of which lie within the technically relevant range:

Clearing point: 85° C., Δε [1 kHz, 20° C.]: −6.0 and $\gamma_1$ [mPa·s, 20° C.]: 390.

What is claimed is:

1. A compound of the formula (I)

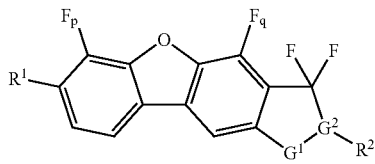

(I)

where:
$R^1$, $R^2$ are each independently
a) H
b) $-M^1-A^1-R^5$
c) a straight-chain or branched alkyl radical having from 1 to 16 carbon atoms or a straight-chain or branched alkenyl radical having from 2 to 16 carbon atoms, where
  c1) one or more nonadjacent and nonterminal $CH_2$ groups may be replaced by —O—, —C(=O)O—, —O—C(=O)—, —O—C(=O)—O—, —C(=O)— or —Si(CH$_3$)$_2$—, and/or
  c2) one $CH_2$ group may be replaced by —C≡C—, cyclopropane-1,2-diyl, cyclobutane-1,3-diyl, cyclohexane-1,4-diyl or phenylene-1,4-diyl, and/or
  c3) one or more hydrogen atoms may be replaced by F and/or Cl,
p, q are each independently 0 or 1
$G^1$-$G^2$ is —CH$_2$CH—, —CH=C—, —CH$_2$CH$_2$CH— or —CH=CH—CH—
$M^1$ is —CO—O—, —O—CO—, —CH$_2$—O—, —O—CH$_2$—, —CF$_2$—O—, —O—CF$_2$—, —CH=CH—, —CF=CF—, —C≡C—, —CH$_2$—CH$_2$—CO—O—, —O—CO—CH$_2$—CH$_2$—, —CH$_2$—CH$_2$—, —CF$_2$—CF$_2$—, —(CH$_2$)$_4$—, —OC(=O)CF=CF— or a single bond,
$A^1$ is 1,4-phenylene where one or two hydrogen atoms may be replaced by F, Cl, CN and/or OCF$_3$, or up to three hydrogen atoms may be replaced by fluorine, 1,4-cyclohexylene where one or two hydrogen atoms may be replaced by CH$_3$ and/or F, 1-cyclohexene-1,4-diyl, where one hydrogen atom may be replaced by CH$_3$ or F, or 1,3-dioxane-2,5-diyl,
$R^5$ has the same possible definitions as $R^1$ and $R^2$, with the exception of $-M^1-A^1-R^5$
with the provisos that:
a) at least one of p, q is 1,
b) $R^1$ and $R^2$ must not at the same time be H.

2. A compound as claimed in claim 1, which corresponds to one of the formulae (Ia1) or (Ia2)

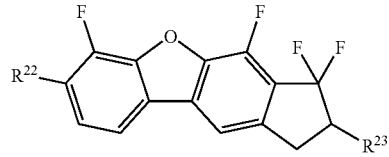

(Ia1)

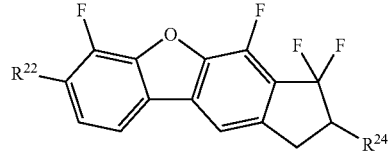

(Ia2)

where:
$R^{22}$ and $R^{23}$ are each independently an alkyl or alkyloxy radical having from 1 to 6 carbon atoms or an alkenyl or alkenyloxy radical having from 2 to 5 carbon atoms,
$R^{24}$ is the $R^{15}$-$A^{15}$-$M^{15}$-moiety where
$R^{15}$ is an alkyl or alkyloxy radical having from 1 to 10 carbon atoms or an alkenyl or alkenyloxy radical having from 2 to 10 carbon atoms,
$A^{15}$ is phenylene-1,4-diyl, cyclohexane-1,4-diyl,
$M^{15}$ is a single bond or —CH$_2$CH$_2$—.

3. A liquid-crystal mixture, which comprises one or more compounds of the formula (I) as claimed in claim 1.

4. The liquid-crystal mixture as claimed in claim 3, which comprises one or more compounds of the formula (I) in an amount of from 1 to 40% by weight, based on the liquid-crystal mixture.

5. The liquid-crystal mixture as claimed in claim 3, which comprises at least three further components of smectic and/or nematic and/or cholesteric phases.

6. The liquid-crystal mixture as claimed in claim 3, which is chiral-smectic.

7. The liquid-crystal mixture as claimed in claim 3, which is nematic or cholesteric.

8. A liquid-crystal display comprising the liquid-crystal mixture as claimed in claim 3.

9. The liquid-crystal display as claimed in claim 8, which is operated in ECB, IPS or VA display mode and comprises the nematic or cholesteric liquid-crystal mixture.

* * * * *